United States Patent
Kim et al.

(10) Patent No.: US 9,604,929 B2
(45) Date of Patent: Mar. 28, 2017

(54) FUNCTIONALIZED CARBON NANOPARTICLES AND FUNCTIONAL POLYMER FIBERS PREPARED USING THE SAME

(71) Applicant: Kyungpook National University Industry-Academic Cooperation Foundation, Daegu (KR)

(72) Inventors: Youngkyoo Kim, Daegu (KR); Hwajeong Kim, Daegu (KR)

(73) Assignee: Kyungpook National University Industry-Academic Cooperation Foundation (KR)

( * ) Notice: Subject to any disclaimer, the term of this patent is extended or adjusted under 35 U.S.C. 154(b) by 127 days.

(21) Appl. No.: 14/481,104

(22) Filed: Sep. 9, 2014

(65) Prior Publication Data
US 2015/0204009 A1 Jul. 23, 2015

(30) Foreign Application Priority Data
Jan. 21, 2014 (KR) .................. 10-2014-0007163

(51) Int. Cl.
*D06M 13/355* (2006.01)
*C07D 213/04* (2006.01)
*D06M 11/74* (2006.01)
*D06M 13/00* (2006.01)
*D06M 13/144* (2006.01)
*D06M 13/35* (2006.01)
*D06M 23/08* (2006.01)
*D06M 101/32* (2006.01)
*D06M 101/34* (2006.01)

(52) U.S. Cl.
CPC .......... *C07D 213/04* (2013.01); *D06M 11/74* (2013.01); *D06M 13/005* (2013.01); *D06M 13/144* (2013.01); *D06M 13/35* (2013.01); *D06M 23/08* (2013.01); *D06M 2101/32* (2013.01); *D06M 2101/34* (2013.01)

(58) Field of Classification Search
None
See application file for complete search history.

(56) References Cited

U.S. PATENT DOCUMENTS

2003/0201051 A1* 10/2003 Hansen .................. A61L 15/60
  156/62.2
2011/0204297 A1* 8/2011 Park ........................ H01B 1/24
  252/503
2012/0065311 A1* 3/2012 Chakraborty .......... B82Y 30/00
  524/364

OTHER PUBLICATIONS

Gerogakilas et al. "Multipurpose Organically Modified Carbon Nanotubes: From Functionalization to Nanotube Composites", Journal of the American Chemical Society, 130, 8733-8740, Jun. 14, 2008.*
Selvin, "Effect of Phenol Functionalized Carbon Nanotube on Mechanical, Dynamic Mechanical, and Thermal Properties of Isotactic Polypropylene Nanocomposites", Polymer Science and Engineering, 52(3), 525-531 Mar. 2012.*
Kokil et al., "Introduction of Multiple Hydrogen Bonding for Enhanced Mechanical Performance of Polymer-Carbon Nanotube Composites," Journal of Macromolecular Science, Part A: Pure and Applied Chemistry, 48:12, 1016-1021, Nov. 1, 2011.
Kumar et al., "Selective covalent immobilization of catechol on activated carbon electrodes," Journal of Electroanalytical Chemistry, vol. 641, 131-135, Dec. 22, 2009.
Boehm et al., Surface Oxides of Carbon, Angew. Chem. Internat. Edit., vol. 3, No. 10, 1964, pp. 669-677.
Wang et al., "Using Carbon Black Nanoparticles to Dye the Cationic-Modified Cotton Fabrics," Journal of Applied Polymer Science, vol. 124, 2012, pp. 5194-5199.
Grafting onto Carbon Black: Graft Polymerization of β-Propiolactone Onto Carbon Black Surface, Journal of Polymer Science: Polymer Letters Edition, vol. 20, 1982, pp. 27-31.
Lee et al., "Resorcinol-functionalized carbon nanoparticles with a stick-out nanostructure for stable hydrogen bonding with polyester microfibers," RSC Adv., vol. 3, Sep. 10, 2013, pp. 19440-19447.

* cited by examiner

*Primary Examiner* — Randy Gulakowski
*Assistant Examiner* — Christopher M Rodd
(74) *Attorney, Agent, or Firm* — Hovey Williams LLP (57) ABSTRACT

The present invention relates to a functionalized carbon nanoparticle prepared by modifying the surface of a carbon nanoparticle with $C_{5-10}$ aryl or heteroaryl substituted with one or more hydroxyl groups, and a functional polymer fiber bound therewith. The functionalized carbon nanoparticles according to the present invention are tightly bound to the polymer fiber, thereby providing the polymer fiber with the properties of carbon nanoparticle. The properties of the carbon nanoparticle being further provided in addition to those of the polymer fiber, the polymer fiber is expected to further expand its scope of application.

6 Claims, 7 Drawing Sheets

FIG. 1A

Carbon Nanoparticle
($C_{NP}$)

Carbon Nanoparticle with Resorcinols
($C_{NP}$-RC)

C<sub>NP</sub>-RC-bound PET Fabric    C<sub>NP</sub>-RC-bound PET Fiber

FUNCTIONALIZED CARBON NANOPARTICLES AND FUNCTIONAL POLYMER FIBERS PREPARED USING THE SAME

BACKGROUND OF THE INVENTION

1. Related Applications

The present application claims the priority benefit of Korean Patent Application No. 10-2014-0007163, filed on Jan. 21, 2014, incorporated by reference herein.

2. Field of the Invention

The present invention relates to functionalized carbon nanoparticles prepared by modifying the surface of the carbon nanoparticles with $C_{5-10}$ aryl or heteroaryl substituted with one or more hydroxyl groups, and functional polymer fibers bound therewith.

3. Description of the Related Art

All carbon nanomaterials have attracted a keen interest since carbon nanotubes and graphenes emerged as potential functional nanomaterials. The presence of π-orbitals and long conjugated structures in these carbon nanomaterials make possible various functionality, such as electrical conductance, chemical reaction sites, black color, etc. In particular, most carbon nanomaterials exhibit outstanding physicochemical and mechanical stabilities compared to other organic materials. Given this, carbon nanomaterials have been utilized as electronic materials in various applications.

Of all these carbon nanomaterials, carbon nanoparticles (CNPs), so-called graphites or carbon blacks, have also been widely used for electrode materials, anti-static materials, additives for tires and paints, etc., through physical mixing techniques. However, minimal attention has been paid to the binding of carbon nanoparticles to polymer fibers. The carbon nanoparticles are basically hydrophobic and thus they aggregate or agglomerate in water, whereas the widely used polymer fibers, such as polyesters, polyamides, polyketones, etc., have polar groups. For this reason, the binding of carbon nanoparticles to polymer fibers is restricted.

However, the binding of carbon nanoparticles to polymer fibers provides the functionality of carbon nanoparticles in addition to that of polymer fibers, and thus is useful for the development of functional fibers. Accordingly, technology for improving the binding of carbon nanoparticles to polymer fibers is required.

Conventionally, the use of dispersing agents such as a sodium salt of polynaphthalene sulfonic acid has been suggested (C. Wang, X. Zhang, F. Lv and L. Peng, J. Appl. Poly. Sci., 2012, 124, 5194). However, this method cannot resolve the intrinsic issue of the carbon nanoparticles in relation to their degree of dispersion and stability in water. Theoretically, a strong base (e.g., NaOH) may be employed to form hydroxyl groups on the surface of carbon nanoparticles as reported in several literatures (N. Tsubokawa, A. Funaki, Y. Hada and Y. Sone, J. Polym. Sci., Polym. Lett. Ed., 1982, 20, 27; D. D. H.-P. Boehm, D. E. Diehl, D. C. W. Heck and D. C. R. Sappok, Angew. Chem., Int. Ed. Engl., 1964, 3, 669). Unfortunately, this method also has a drawback in the separation of unreacted strong base that can cause significant damage to the polymer surface. In addition, the interaction between the formed hydroxyl groups in the carbon nanoparticles and the polar groups in the polymer chain is actually unstable because hydroxyl groups are much smaller in size relative to the carbon nanoparticles.

Accordingly, the present inventors have made extensive efforts to develop a method for introducing carbon nanoparticles to polymer fibers. As a result, they found that functionalized carbon nanoparticles whose surfaces are modified with $C_{5-10}$ aryl or heteroaryl substituted with one or more hydroxyl groups can excellently bind to polymer fibers, thereby completing the present invention.

SUMMARY OF THE INVENTION

An object of the present invention is to provide functionalized carbon nanoparticles prepared by modifying the surface of carbon nanoparticles with $C_{5-10}$ aryl or heteroaryl substituted with one or more hydroxyl groups, in order to introduce the carbon nanoparticles onto polymer fibers.

Another object of the present invention is to provide a functional polymer fiber bound with the functionalized carbon nanoparticles.

DETAILED DESCRIPTION OF THE PREFERRED EMBODIMENTS

In order to achieve the above objects, the present invention provides functionalized carbon nanoparticles prepared by modifying the surface of carbon nanoparticles with $C_{5-10}$ aryl or heteroaryl substituted with one or more hydroxyl groups.

As used herein, the term "carbon nanoparticles" refers to nanoparticles composed of carbon atoms, characterized by having π-orbitals and long conjugated structures. In the present invention, the carbon nanoparticles may be preferably graphite, carbon nanotube, or graphene, in order to introduce functional groups to double bonds of the carbon nanoparticles. Carbon nanoparticles themselves have outstanding physicochemical properties, and thus have been applied to various fields, for example, widely used for electrode materials, anti-static materials, additives for tires and paints, or the like. However, carbon nanoparticles are basically hydrophobic and thus they aggregate or agglomerate in water. For this reason, it is hardly used together with hydrophilic substances, and thus there is a limit in its application.

In particular, the present invention is intended to introduce carbon nanoparticles to polymer fibers. However, the widely used polymer fibers, for example, polyesters, polyamides, polyketones, etc., have polar groups, and therefore, introduction of carbon nanoparticles to these polymer fibers themselves is restricted.

Accordingly, the present invention is intended to facilitate introduction of carbon nanoparticles to polymer fibers by modifying the surface of carbon nanoparticles, in particular, by introducing hydroxyl groups to carbon nanoparticles to allow hydrogen bonding between the hydroxyl groups and polar groups (e.g., carbonyl group) of the polymer fibers.

For introduction of hydroxyl groups to carbon nanoparticles, the present invention is characterized in that the surface of a carbon nanoparticle is modified with $C_{5-10}$ aryl or heteroaryl substituted with one or more hydroxyl groups.

When $C_{5-10}$ aryl or heteroaryl substituted with one or more hydroxyl groups is introduced to carbon nanoparticles, hydrogen bonding can be formed between the hydroxyl groups and the polar groups (e.g., carbonyl group) of the polymer fiber, resulting in binding of the carbon nanoparticles to the polymer fiber. The modification may be carried out by using a $C_{5-10}$ aryl or heteroaryl compound substituted with one or more hydroxyl groups, which further comprises halogen groups. For example, when the $C_{5-10}$ aryl or heteroaryl compound substituted with one or more hydroxyl groups, which further comprises halogen groups, is used for the modification, $C_{5-10}$ aryl or heteroaryl substituted with one or more hydroxyl groups can be introduced to carbon nanoparticles by atom transfer radical reaction (ATRR) between the halogen and the double bonds of carbon nanoparticles. Preferably, the halogen group may be Br or Cl. The halogen group dissociates into its radical species, which react with double bonds of carbon nanoparticles, thereby stabilizing the radical structure of $C_{5-10}$ aryl or heteroaryl. In addition, one or more hydroxyl groups are preferred, and one hydroxyl group undergoes direct hydrogen bonding with the polar group of the polymer fiber. Two or more hydroxyl groups may be preferred.

Further, $C_{5-10}$ aryl is preferably phenyl.

More preferably, the $C_{5-10}$ aryl or heteroaryl compound substituted with one or more hydroxyl groups may be 2,4-dihydroxyphenyl; 2-bromophenol; 2,4,6-tribromophenol; 2-bromo-4-chlorophenol; 2-bromo-3-methoxyphenol; 2,4,6-tribromo-5-methyl-1,3-benzenediol; 2-bromo-5-methylhydroquinone; 2-bromo-5-nitrophenol; 3,5-dibromo-2,4-dihydroxybenzoic acid; 3'-bromo-5'-chloro-2'-hydroxychalcone; 2,6-dibromophenol; 2,4-dibromophenol; 1-bromo-2-naphtol; bromohydroquinone; 3-bromo-2-naphtol; 1,6-dibromo-2-naphtol; 3-bromocatechol; 2,6-dibromo-1,5-dihydroxynaphthalene; 2,5-dibromohydroquinone; 2,4,6-tribromoresorcinol; 2,4-dibromo-1-naphtol; tetrabromohydroquinone; 2-bromo-4-chlorophenol; 2-bromo-p-cresol; 2-bromo-4-fluorophenol; 2-bromo-4-methoxyphenol; 6-bromo-o-cresol; 2,6-dibromo-p-cresol; 2,6-dibromo-4-fluorophenol; 3-bromo-4-hydroxybenzonitrile; 3-bromo-4-hydroxybenzaldehyde; 2-bromo-4-tert-butylphenol; 3,5-dibromo-4-hydroxybenzaldehyde; 2,3,5,6-tetrabromo-p-cresol; 3-bromosalicylaldehyde; α,3,5-tribromo-2-hydroxytoluene; 3,5-dibromosalicylaldehyde; 3',5'-dibromo-4'-hydroxyacetophenone; 3,3'-dibromo-4,4'-biphenol; 2,6-dibromo-4-nitrophenol; methyl 4-bromo-3-hydroxybenzoate; 4,7-dibromo-3-hydroxy-2-naphthoic acid; 5,7-dibromo-8-hydroxyquinoline; or 7-bromo-5-chloro-8-hydroxyquinoline.

Such functionalized carbon nanoparticles have a hydrophilic property instead of a hydrophobic property, due to introduction of hydroxyl groups. According to an embodiment of the present invention, it can be confirmed that functionalized carbon nanoparticles according to the present invention are well dispersed in water and not agglomerated, whereas carbon nanoparticles before functionalization are hardly dispersed in water.

Further, the introduced hydroxyl group undergoes hydrogen bonding with the polar group of the polymer fiber, and thus stably binds to the surface of polymer fiber. According to an embodiment of the present invention, it can be confirmed that the mixing of the functionalized carbon nanoparticles according to the present invention and the polymer fiber leads to stable binding of the functionalized carbon nanoparticles to the surface of the polymer fibers.

For more detailed explanation, the present invention will be described with reference to FIGS. 1A and 1B, which illustrate an embodiment of the present invention.

Figure 1A:
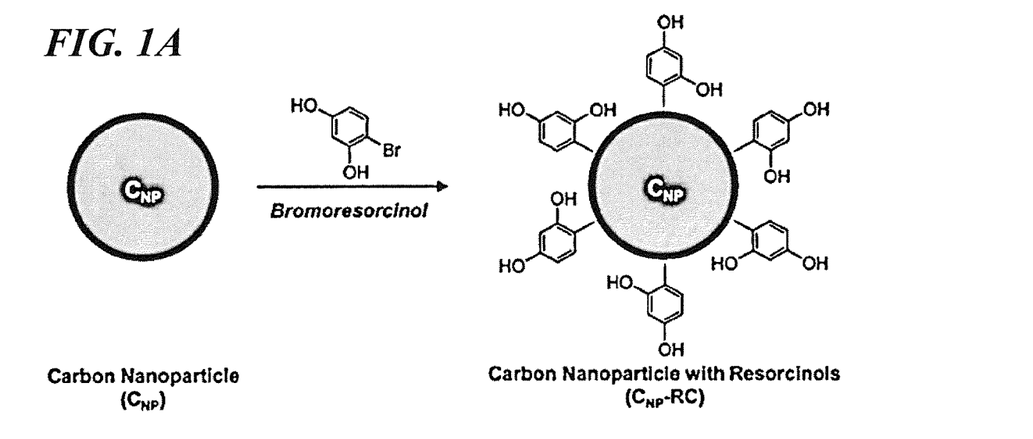
FIG. 1A shows a structure of the carbon nanoparticle before and after preparation of the functionalized carbon nanoparticle according to an embodiment of the present invention.

As shown in FIG. 1A, hydroxyl groups can be introduced to the surface of carbon nanoparticles by reaction between carbon nanoparticles and $C_{5-10}$ aryl or heteroaryl substituted with one or more hydroxyl groups (bromoresorcinol in FIG. 1A). A plurality of hydroxyl groups are introduced to the surface of a carbon nanoparticle, which features a structure like a chestnut burr, and thus is effective for the reaction with polar groups of the polymer fiber.

Figure 1B:
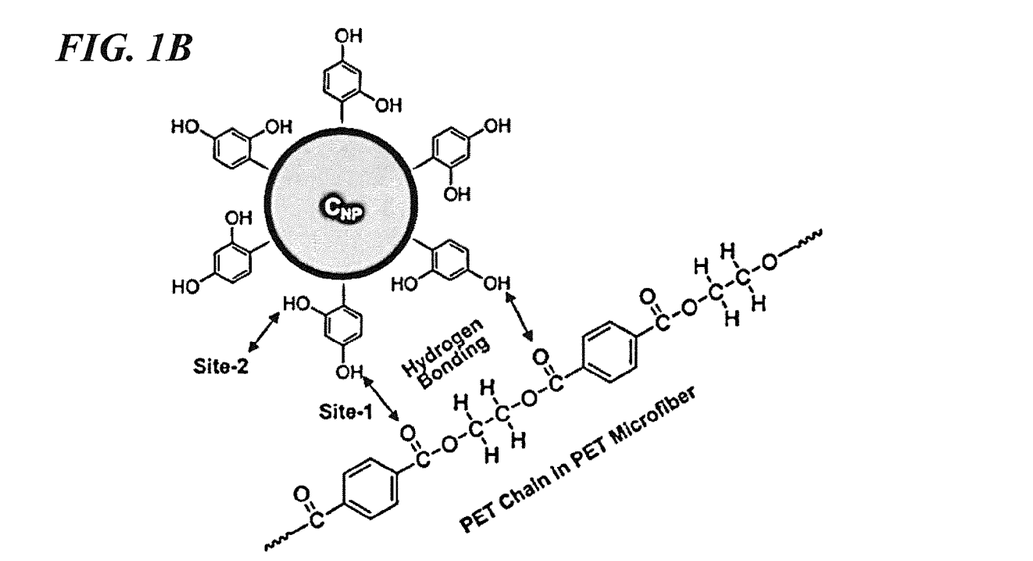
FIG. 1B shows a schematic diagram of the functionalized carbon nanoparticle binding with a polymer fiber.

As shown in FIG. 1B, the hydroxyl groups of the functionalized carbon nanoparticles form a hydrogen bond with the polar groups of the polymer fiber (carbonyl group of PET fiber in FIG. 1B), leading to an excellent introduction of carbon nanoparticles to the polymer fiber.

There is no limitation on the polymer fibers to be used, as long as they are fibers composed of a polymer having polar groups. In the present invention, the polymer fibers may be preferably polyester fibers, polyamide fibers, or polyketone fibers.

Further, the present invention provides a method for preparing the functionalized carbon nanoparticles, including the step of reacting a carbon nanoparticle with a $C_{5-10}$ aryl halogenated compound or a heteroaryl halogenated compound substituted with two or more hydroxyl groups.

The reaction is an atom transfer radical reaction (ATRR) using radicals which are generated during leaving of halogen from the aryl halogenated compound or the heteroaryl halogenated compound. To generate radicals, CuBr and 2,2'-bipyridine are preferably used as catalysts. Toluene is preferably used as a solvent.

For more detailed description, it will be described with reference to FIGS. 2A-2C, which illustrate an embodiment of the present invention.

Figure 2A:
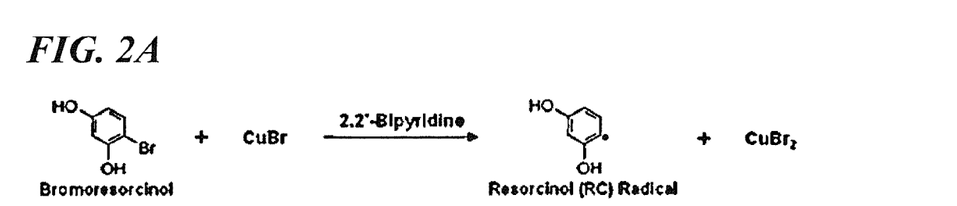
FIG. 2A shows bromoresorcinol dissociating into the resorcinol radical according to an embodiment of the present invention.
Figure 2B:
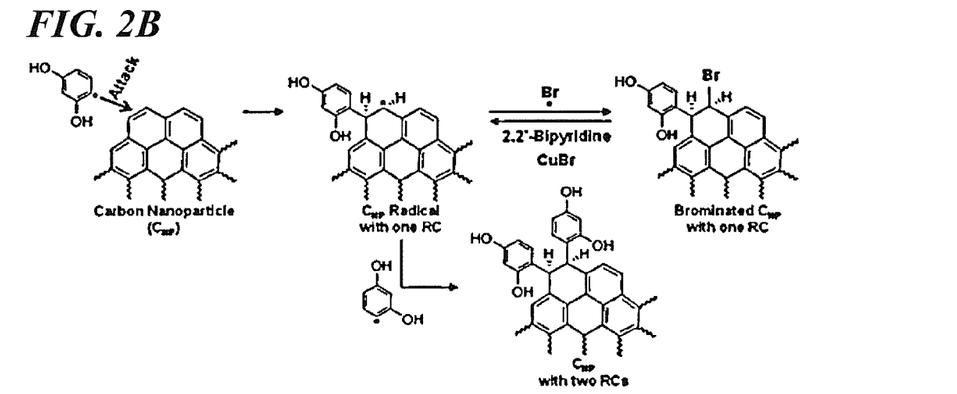
FIG. 2B shows a preparation process of the functionalized carbon nanoparticle according to an embodiment of the present invention.
Figure 2C:
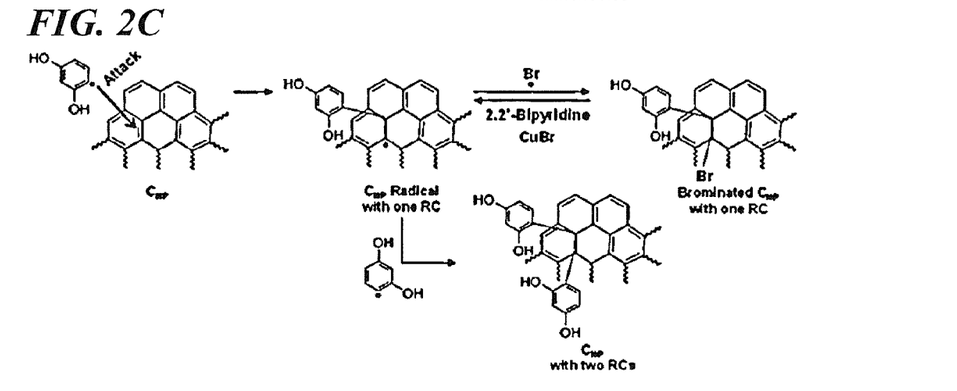
FIG. 2C shows a preparation process of the functionalized carbon nanoparticle according to another embodiment of the present invention.

As shown in FIG. 2A, bromoresorcinol first dissociates into the resorcinol radical and the bromine radical, and the bromine radical reacts with CuBr, leading to formation of $CuBr_2$. Then, as shown in FIG. 2B, the resorcinol radical attacks a double bond (—CH═CH—) on the surface (edge part) of carbon nanoparticle, which results that the resorcinol group is covalently bonded to the surface of the carbon nanoparticle while, at the same time, a new radical is created in a neighboring carbon on the surface of the carbon nanoparticle. Finally, the new radical site is sufficiently reactive with another resorcinol, leading to binding of a carbon nanoparticle with two resorcinol groups. Further, some bromine radicals before reacting with CuBr can also react with the radical on the surface of the carbon nanoparticle, but these bromine groups on the surface of the carbon nanoparticle are subjected to a similar dissociation process by the catalyst (right part of FIG. 2B). As shown in FIG. 2C, a similar ATRR process is possible for the double bonds without hydrogen inside the carbon nanoparticles.

Further, the present invention provides a functional polymer fiber bound with the functionalized carbon nanoparticles.

As described above, the functionalized carbon nanoparticles according to the present invention are tightly bound to the polymer fiber, thereby providing the polymer fiber with the properties of a carbon nanoparticle. That is, the polymer fiber can be provided with an anti-static effect, a deodorizing effect, an electrical conductance, etc. of the carbon nanoparticle. The properties of the carbon nanoparticle being further provided in addition to that of the polymer fiber, the polymer fiber is expected to further expand its scope of application.

Hereinafter, the preferred Examples are provided for better understanding of the present invention. However, these Examples are for illustrative purposes only, and the invention is not intended to be limited by these Examples.

In the following Examples, carbon nanoparticles were purchased from Korea Carbon Black Co., Ltd. and used after washing with toluene (Junsei, purity=99.5%). The PET polymer (degree of polymerization=100; weight-average molecular weight=19,200) fibers were purchased from Handeok Textile Inc. Bromoresorcinol (Tokyo Chemical Ind., purity=98%), CuBr (Sigma-Aldrich, purity=98%), and 2,2'-bipyridine (Tokyo Chemical Ind., purity=99%) were purchased and used without further purification.

EXAMPLE 1

Preparation of Functionalized Carbon Nanoparticles

To prepare functionalized carbon nanoparticles, CuBr (0.574 g) and 2,2'-bipyridine (1.25 g) were added to toluene (150 ml) and the mixture was stirred at room temperature to be well dispersed. The resulting solution was added with carbon nanoparticles (0.288 g) and bromoresorcinol (0.756 g) and then heated up to the reflux temperature of toluene (about 110° C.). The reaction was continued for 48 hours under reflux conditions. After cooling the solution to room temperature, the product was filtered and subsequently washed with excess toluene thoroughly to remove the remaining 2,2-bipyridine. The washed product was dried under vacuum overnight at 100° C. Next, the dried product was dispersed in N,N-dimethylacetamide (DMAc, 50 mL) and subjected to ultrasonication for 30 minutes to dissolve the functionalized carbon nanoparticles and the ionized copper catalyst. The dissolved black solution was centrifuged at 14,000 rpm for 20 minutes to precipitate only the functionalized carbon nanoparticles and repeatedly washed with DMAc and water for complete removal of the remaining catalyst. Finally, the separated product (functionalized carbon nanoparticles) was dried under vacuum for 24 hours at 100° C.

EXAMPLE 2

Preparation of PET Fiber Introduced with Functionalized Carbon Nanoparticles

The functionalized carbon nanoparticles prepared in Example 1 were dispersed in water at various concentrations (6, 8, and 10 wt %) to examine concentration effects. The PET fibers were soaked in the aqueous solutions, in which the functionalized carbon nanoparticles were dispersed at three different concentrations, and heated up to 130° C. for 40 minutes. Then, the PET fibers were examined with the naked eye. As a result, the darkest color was observed at 10 wt %, and used in the following experiment.

The PET fibers were soaked in an aqueous solution, in which the functionalized carbon nanoparticles were dispersed at a concentration of 10 wt %, by the following three soaking methods:

1) Soaking method-1: heating the functionalized carbon nanoparticle-dispersed aqueous solution from room temperature to 130° C. for 100 minutes and then soaking the PET fiber for 40 minutes (i.e., soaking after heating);

2) Soaking method-2: soaking the PET fiber in the functionalized carbon nanoparticle-dispersed aqueous solution, and then heating it from room temperature to 130° C. for 140 minutes (i.e., heating while soaking); and 3) Soaking method-3: soaking the PET fiber in the functionalized carbon nanoparticle-dispersed aqueous solution, and then heating it from room temperature to 130° C. for 140 minutes, and drying the PET fiber at room temperature and this process was repeated one more time (i.e., double soaking-heating, total soaking time=280 minutes).

After finishing the soaking tests, all fiber samples were finally dried in air. In order to investigate whether the functionalized carbon nanoparticles were tightly bound to the surface of each PET microfiber, single PET microfibers were carefully taken out of each PET fiber and loaded into a vacuum chamber for SEM measurements.

EXPERIMENTAL EXAMPLE 1

NMR Spectroscopy

Figure 3:
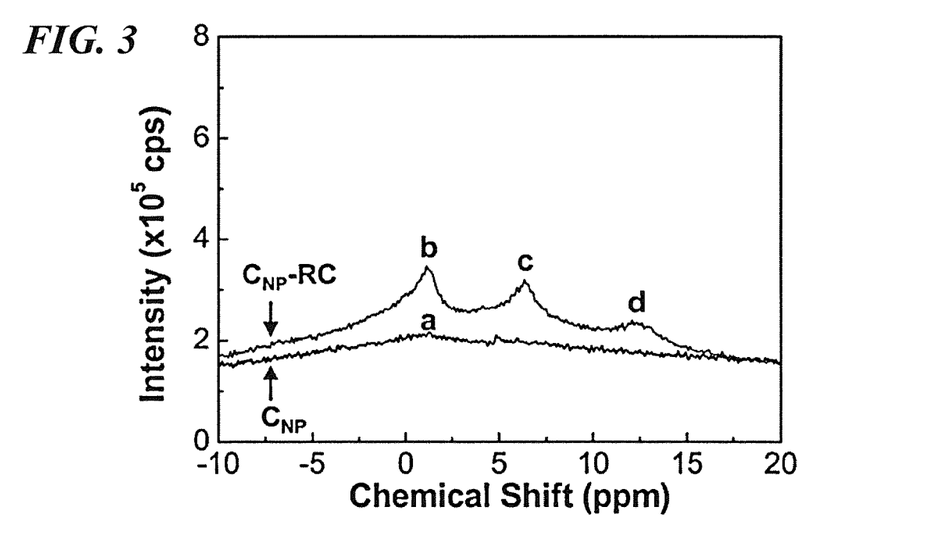
FIG. 3 shows NMR results of the carbon nanoparticles according to an embodiment of the present invention, in which CNP indicates carbon nanoparticles and CNP-RC indicates the functionalized carbon nanoparticles according to an embodiment of the present invention.

The functionalized carbon nanoparticles prepared in Example 1 were characterized by NMR spectroscopy (1H-FT-NMR, 600 MHz, Varian UNITY INOVA), and the result is shown in FIG. 3.

As shown in FIG. 3, a weak broad peak was observed at 1.13 ppm for the aliphatic protons in the original carbon nanoparticles ('a.' in FIG. 3), which can be attributed to the protons in the edge parts (—CH═CH—) of the original carbon nanoparticles. In addition, it was considered that this broad peak might include methylene (—$CH_2$—) or alkyl (—$CH_3$) groups which are formed by natural degradation during the preparation process of CNP or upon exposure to air ambient conditions. In contrast, the functionalized carbon nanoparticles exhibited a peak at 1.13 ppm and two additional peaks at 6.34 ppm and 12.08 ppm. The peak at 6.34 ppm is assigned to the protons in the benzene ring of resorcinol, while the peak at 12.08 ppm represents the protons of the hydroxyl groups of resorcinol. Therefore, it was confirmed that the resorcinol groups were introduced to the surface of the carbon nanoparticles.

EXPERIMENTAL EXAMPLE 2

Raman Spectroscopy

Figure 4:
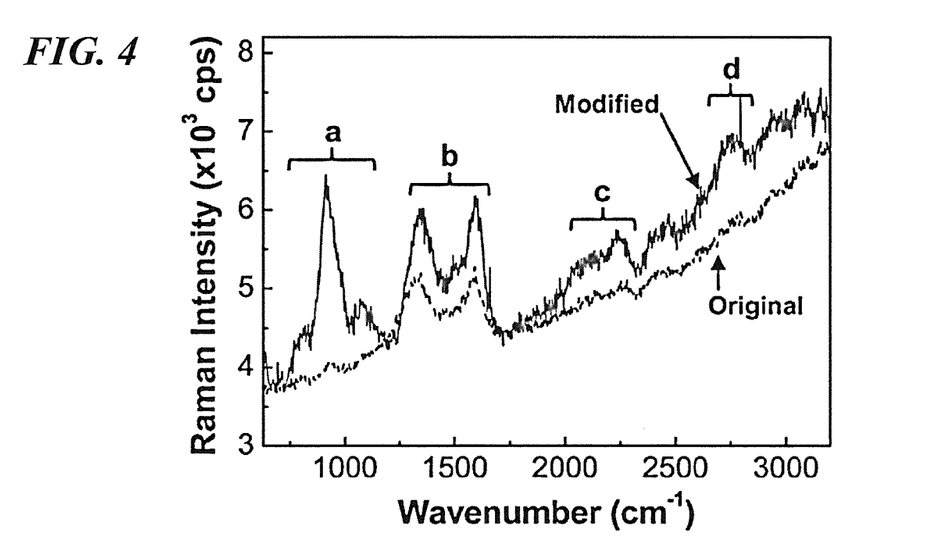
FIG. 4 shows the result of Raman spectroscopy of the carbon nanoparticles according to an embodiment of the present invention.

The functionalized carbon nanoparticles prepared in Example 1 were characterized by Raman spectroscopy (Almega X, Thermo; excitation wavelength=780 nm), and the result is shown in FIG. 4.

As shown in FIG. 4, the original carbon nanoparticles showed two representative peaks, a D peak (C—H bending) at 1360 $cm^{-1}$ and a G peak (C—C stretching) at 1580 $cm^{-1}$ (see 'b' of FIG. 4), corresponding to benzenoid structures in the presence of weak G* and 2D peaks (aliphatic C—H) at above 2000 $cm^{-1}$ (see 'c' and 'd' of FIG. 4). These peaks were also found in the functionalized carbon nanoparticles, indicating the good conservation of the original structure of carbon nanoparticles after ATRR process. A strong Raman peak for the phenolic hydroxyl groups at around 920 $cm^{-1}$ (see 'a' in FIG. 4) was observed in the functionalized carbon nanoparticles, indicating the presence of resorcinol groups on the surface of the carbon nanoparticles.

EXPERIMENTAL EXAMPLE 3

Dispersion Stability in Water

The dispersion stability in water was compared between the carbon nanoparticles and the functionalized carbon nanoparticles (Example 1). After adding each sample to water at a solid concentration of 3 mg/6 ml (sample weight/water volume), the mixture solutions were shaken and subjected to ultrasonication. Then, the solutions were left at room temperature for a predetermined period of time, and examined with the naked eye. The result is shown in FIG. 5.

Figure 5:
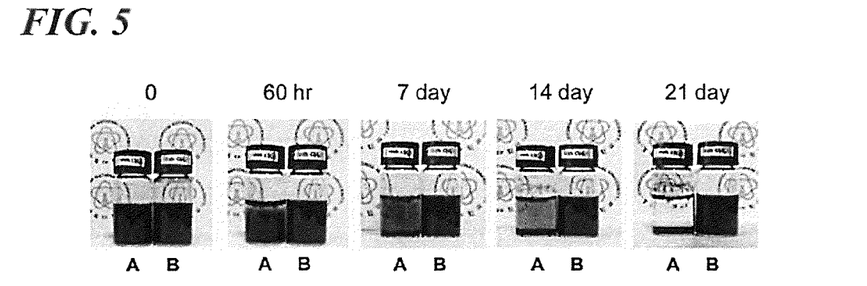
FIG. 5 shows the result of dispersion stability in water according to an embodiment of the present invention, in which A indicates carbon nanoparticles and B indicates the functionalized carbon nanoparticles according to an embodiment of the present invention.

As shown in FIG. 5, both solutions seemed to be well dispersed in water, but after 60 hours, agglomeration was detected in carbon nanoparticles. The agglomeration became more pronounced after 7 days, and after 21 days almost all the carbon nanoparticles were agglomerated. In contrast, no agglomeration was observed in the functionalized carbon nanoparticles even after 21 days. No agglomeration was observed even after 6 months, which is not shown in FIG. 5. This result suggests that the functionalized carbon nanoparticles exhibit an excellent dispersion stability in water.

EXPERIMENTAL EXAMPLE 4

HRTEM

Figure 6A:
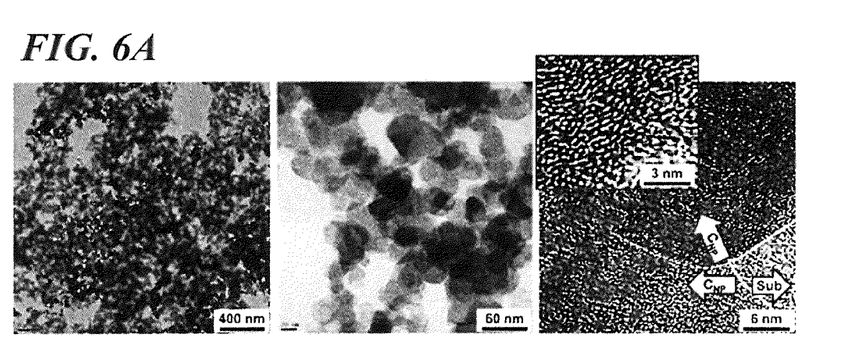
FIG. 6A shows HRTEM images of the carbon nanoparticles according to an embodiment of the present invention.
Figure 6B:
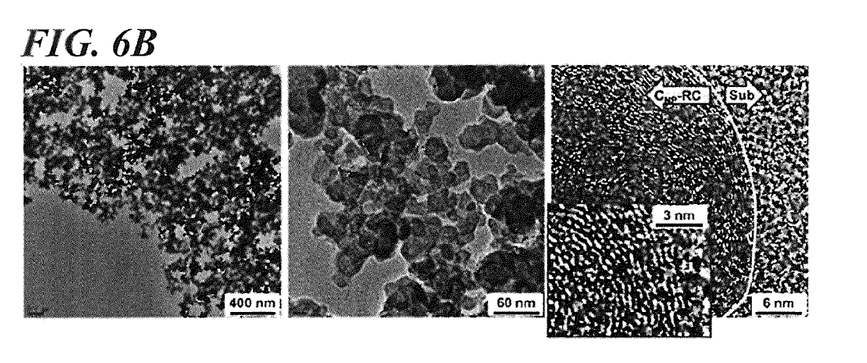
FIG. 6B shows HRTEM images of the functionalized carbon nanoparticles according to an embodiment of the present invention.

The shapes of the carbon nanoparticles and the functionalized carbon nanoparticles (Example 1) were examined by HRTEM (H-7600, Hitachi, Ltd.) and the result is shown in FIGS. 6A and 6B.

As shown in FIG. 6A, several tiny nanoparticles were observed from the original carbon nanoparticle sample (left image of FIG. 6A) and their shape was spherical as expected (middle image of FIG. 6A). The same nanoparticle shape was also observed in the functionalized carbon nanoparticles (left and middle images of FIG. 6B), indicating that the shape of the carbon nanoparticles has been well conserved even after ATRR process. In particular, it was found that the fine lattice nanostructure inside a single carbon nanoparticle was not destructed in the functionalized carbon nanoparticles, indicating that the ATRR process did indeed affect only the surface of the carbon nanoparticle.

EXPERIMENTAL EXAMPLE 5

SEM

In order to examine the extent of the functionalized carbon nanoparticles' binding to the PET microfibers, the following experiment was carried out. First, the optimum concentration of the functionalized carbon nanoparticles dispersed in water was found to be 10 wt %, as in Example 2. Based on this result, three soaking methods as in Example 2 were applied, and each sample was examined by SEM (SUPRA-55VP, ZEISS & Kleindiek) and the result is shown in FIG. 7.

Figure 7:
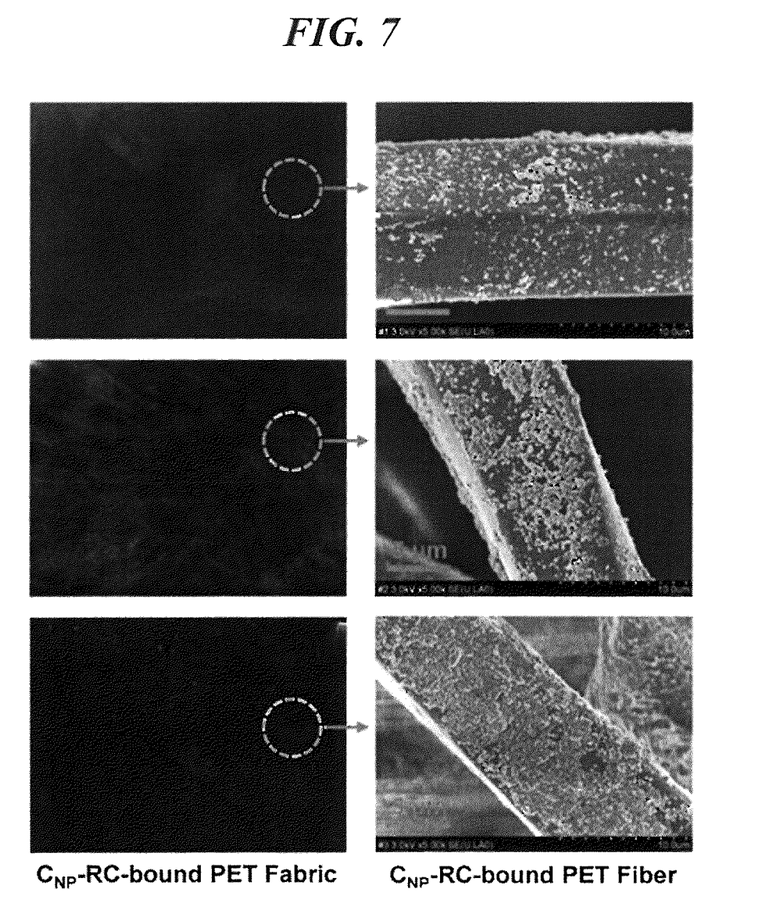
FIG. 7 shows SEM images of the PET fiber bound with the functionalized carbon nanoparticles according to an embodiment of the present invention.

As shown in the left images of FIG. 7, all PET fibers display a black color although the original PET fibers were white. This result indicates that functionalized carbon nanoparticles are actually tightly bound to the PET fibers. However, the amount of the functionalized carbon nanoparticles bound thereto was different (right images of FIG. 7). In soaking method-1 of Example 2, the amount bound was low. However, in soaking method-2 of Example 2, the amount bound was noticeably increased, and in soaking method-3 of Example 2, the amount bound was further increased.

EXPERIMENTAL EXAMPLE 6

Fastness and Rubbing Fastness

Figure 8A:
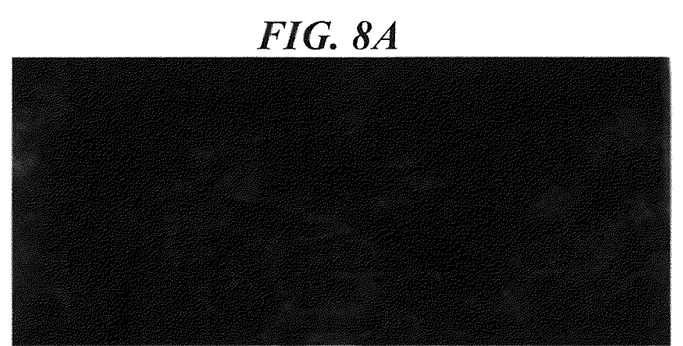
FIG. 8A shows the PET fiber bound with the functionalized carbon nanoparticles according to an embodiment of the present invention before the fastness test.
Figure 8B:
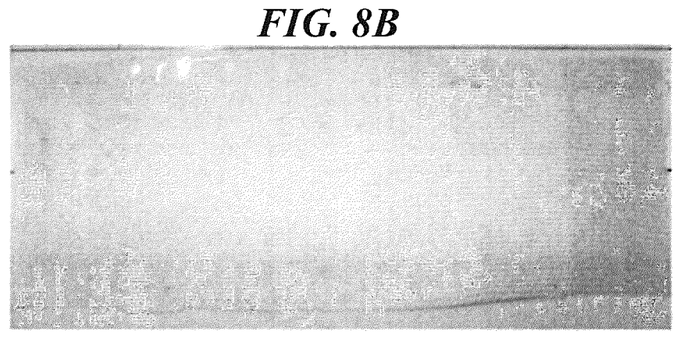
FIG. 8B shows the result of the fastness test.

FIG. 8A shows the PET fiber bound with the functionalized carbon nanoparticles before the fastness test. The fastness test was carried out for the functionalized carbon nanoparticle-bound PET fibers (15×15 cm; Example 2) soaked in 100 ml of a detergent solution (concentration=10 $gL^{-1}$) at 40° C. for 30 minutes (protocol=KS K0430 method) using a Launder-O-Meter. In detail, functionalized carbon nanoparticle-bound PET fibers and the original PET fibers were put in clean water, and stirred at 40° C. for 30 minutes. As shown in FIG. 8B, the color of the original white PET fiber was well maintained, indicating that the functionalized carbon nanoparticles were tightly bound to the PET fibers and not released during normal washing conditions in water.

Figure 8C:
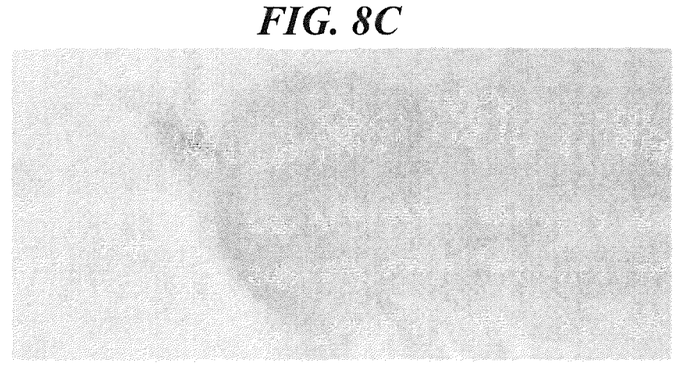
FIG. 8C shows the result of the rubbing fastness test.

In addition, the rubbing fastness test was carried out on functionalized carbon nanoparticle-bound PET fibers (A4 size; Example 2) by direct contact with original PET fibers, upon rubbing with a constant pressure using a crock meter (Daeshin Instrument Co.). As shown in FIG. 8C, the original PET fiber exhibited no black contamination after the rubbing test, indicating that the functionalized carbon nanoparticles are tightly bound to the PET fibers because there is no release of functionalized carbon nanoparticles during washing in water and rubbing.

EXPERIMENTAL EXAMPLE 7

Deodorization Test

The deodorization test was conducted using a functionalized carbon nanoparticle-bound PET fiber (10×20 cm; Example 2) that was inserted in a 2 L flask with an aqueous ammonia solution (5.5 ml). The deodorization rate (%) was calculated by the following Equation:

$$[(C_B-C_S)/C_B] \times 100$$

wherein $C_B$ represents an ammonia gas concentration without the functionalized carbon nanoparticle-bound PET fiber, and $C_S$ represents an ammonia gas concentration with the functionalized carbon nanoparticle-bound PET fiber.

Figure 9:
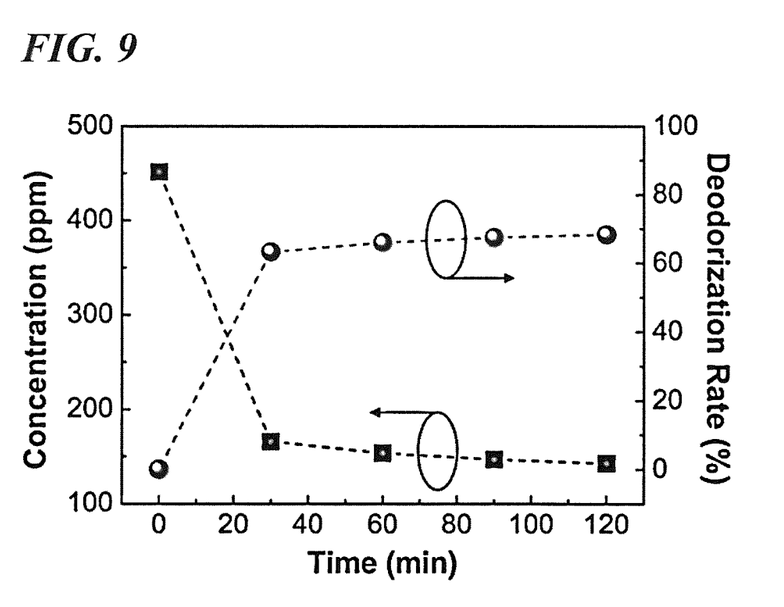
FIG. 9 is a graph showing the deodorization test result of the PET fiber bound with the functionalized carbon nanoparticles according to an embodiment of the present invention.

The ammonia concentration was measured using a Fourier Transform-Infrared gas analyzer (FTS-45, Bio-Rad in Korea Textile Development Ind.), and the result is shown in FIG. 9.

As shown in FIG. 9, the ammonia gas concentration was significantly decreased after 30 min with a deodorization rate of about 65%. Then, the deodorization rate was slightly increased over time.

EFFECT OF THE INVENTION

The functionalized carbon nanoparticles according to the present invention are tightly bound to the polymer fiber, thereby providing a polymer fiber with the properties of carbon nanoparticles. The properties of the carbon nanoparticle being further provided in addition to those of the polymer fiber, the polymer fiber is expected to further expand its scope of application.

What is claimed is:

1. A functionalized carbon nanoparticle prepared by modifying the surface of a carbon nanoparticle with 2,4-dihydroxyphenyl, 2-bromophenol; 2,4,6-tribromophenol; 2-bromo-4-chlorophenol; 2-bromo-3-methoxyphenol; 2,4,6-tribromo-5-methyl-1,3-benzenediol; 2-bromo-5-methyl-hydroquinone; 2-bromo-5-nitrophenol; 3,5-dibromo-2,4-dihydroxybenzoic acid; 3'-bromo-5'-chloro-2'-hydroxychalcone; 2,6-dibromophenol; 2,4-dibromophenol; 1-bromo-2-naphtol; bromohydroquinone; 3-bromo-2-naphtol; 1,6-dibromo-2-naphtol; 3-bromocatechol; 2,6-dibromo-1,5-dihydroxynaphthalene; 2,5-dibromohydroquinone; 2,4,6-tribromoresorcinol; 2,4-dibromo-1-naphtol; tetrabromohydroquinone; 2-bromo-4-chlorophenol; 2-bromo-p-cresol; 2-bromo-4-fluorophenol; 2-bramo-4-methoxyphenol; 6-bromo-o-cresol; 2,6-dibromo-p-cresol; 2,6-dibromo-4-fluorophenol; 3-bromo-4-hydroxybenzonitrile; 3-bromo-4-hydroxybenzaldehyde; 2-bromo-4-tert-butylphenol; 3,5-dibromo-4-hydroxybenzaldehyde; 2,3,5,6-tetrabromo-p-cresol; 3-bromosalicylaldehyde; α,3,5-tribromo-2-hydroxytoluene; 3,5-dibromosalicylaldehyde; 3',5'-dibromo-4'-hydroxyacetophenone; 3,3'-dibromo-4,4'-biphenol; 2,6-dibromo-4-nitrophenol; methyl 4-bromo-3-hydroxybenzoate; 4,7-dibromo-3-hydroxy-2-naphthoic acid; 5,7-dibromo-8-hydroxyquinoline; or 7-bromo-5-chloro-8-hydroxyquinoline.

2. The functionalized carbon nanoparticle according to claim 1, wherein the carbon nanoparticle includes graphite, carbon nanotube, or graphene.

3. A functional polymer fiber comprising the functionalized carbon nanoparticle of claim 1 bound thereto.

4. The functional polymer fiber according to claim 3, wherein the polymer fiber is a polyester fiber, a polyamide fiber, or a polyketone fiber.

5. The functional polymer fiber according to claim 3, wherein the carbon nanoparticle includes graphite, carbon nanotube, or graphene.

6. The functional polymer fiber according to claim 3, wherein the functionalized carbon nanoparticle is bound to a polymer fiber via a hydrogen bond.

\* \* \* \* \*